(12) United States Patent
Sharma et al.

(10) Patent No.: US 11,443,201 B2
(45) Date of Patent: Sep. 13, 2022

(54) ARTIFICIAL INTELLIGENCE-BASED SELF-LEARNING IN MEDICAL IMAGING

(71) Applicant: Siemens Healthcare GmbH, Erlangen (DE)

(72) Inventors: Puneet Sharma, Princeton Junction, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 1151 days.

(21) Appl. No.: 15/984,562

(22) Filed: May 21, 2018

(65) Prior Publication Data
US 2019/0354882 A1 Nov. 21, 2019

(51) Int. Cl.
| | |
|---|---|
| G06F 15/18 | (2006.01) |
| G06N 5/04 | (2006.01) |
| G16H 30/20 | (2018.01) |
| G06T 7/00 | (2017.01) |
| G16H 30/40 | (2018.01) |
| G06N 20/00 | (2019.01) |

(52) U.S. Cl.
CPC .............. *G06N 5/04* (2013.01); *G06N 20/00* (2019.01); *G06T 7/0012* (2013.01); *G16H 30/20* (2018.01); *G16H 30/40* (2018.01); *G06T 2207/20081* (2013.01); *G06T 2207/30004* (2013.01)

(58) Field of Classification Search
CPC ........ G06N 5/04; G06N 20/00; G06N 3/0454; G06N 3/08; G06T 7/0012; G06T 2207/20081; G06T 2207/30004; G06T 2207/20084; G16H 30/20; G16H 30/40; G16H 50/70; A61B 6/032; A61B 6/037
See application file for complete search history.

(56) References Cited

U.S. PATENT DOCUMENTS

| | | | |
|---|---|---|---|
| 9,760,690 B1* | 9/2017 | Petkov | G16H 30/20 |
| 9,918,690 B2* | 3/2018 | Itu | G06T 7/11 |
| 2019/0138693 A1* | 5/2019 | Muller | G06N 3/02 |
| 2019/0139641 A1* | 5/2019 | Itu | G06N 3/0472 |

FOREIGN PATENT DOCUMENTS

| | | | | |
|---|---|---|---|---|
| CN | 107610193 A | * | 1/2018 | G06N 3/02 |

OTHER PUBLICATIONS

U.S. Appl. No. 15/809,802, filed Nov. 10, 2017.

* cited by examiner

*Primary Examiner* — Xin Jia

(57) ABSTRACT

For machine learning for a medical imager, results created for individual patients are used to generate the ground truth. The acceptance or change for examining an individual patient is used as the ground truth instead of using a further expert study for the purposes of machine training. In this way, the medical imager creates both samples and ground truth as part of every-day, on-going examinations of patients in the production environment. Machine training is performed based on these samples, and the machine-learned network may then be applied for imaging further patients. For example, the medical imager self-optimizes or self-learns, allowing for updating the machine-learned network more rapidly (e.g., keeping pace with changes in practice in a lower cost and less time-consuming approach and/or updating localized to a practice) in the production environment.

17 Claims, 2 Drawing Sheets

ARTIFICIAL INTELLIGENCE-BASED SELF-LEARNING IN MEDICAL IMAGING

BACKGROUND

The present embodiments relate to medical imaging. Machine learning-based technology is applied in healthcare imaging. Typically, the machine-learned network is trained from a large training database with ground-truth labels. The process of setting up the training database with curated and annotated ground-truth labels requires considerable time and resources. Many examples are gathered, and experts tediously create the ground truths for the examples. Additionally, researchers are needed to setup experiments to train a model and then deploy it on imaging device (scanner) or a reading and/or post-processing workstation.

The machine learning-based algorithms that are deployed on the medical imaging scanners are trained offline in a controlled setting. Although the scanner is used daily, the deployed machine learning algorithms remain the same despite changes in clinical practice or variances between different practices. Failure cases may be collected in an ad hoc fashion over time and may then be used to re-train the algorithm of interest. The re-trained models are then deployed on the scanner in the production environment, typically in the next software release. The process relies on expertise to create the ground truth in an off-line training process, so is expensive, time consuming, does not keep pace with changes, and does not account for variances in different clinical practices.

SUMMARY

By way of introduction, the preferred embodiments described below include methods, systems, instructions, and computer readable media for machine learning for a medical imager. The results created for individual patients are used to generate the ground truth. The acceptance or change for examining an individual patient is used as the ground truth instead of using a further expert study for the purposes of machine training. In this way, the medical imager creates both samples and ground truth as part of every-day, on-going examinations of patients in the production environment. Machine training is performed based on these samples, and the machine-learned network may then be applied for imaging further patients. For example, the medical imager self-optimizes or self-learns, allowing for updating the machine-learned network more rapidly (e.g., keeping pace with changes in practice in a lower cost and less time-consuming approach and/or updating localized to a practice) in the production environment.

In a first aspect, a method is provided for machine learning with a medical imager. The medical imager acquires first image data representing a first patient and generates a first image of the first patient from the first image data. A ground truth for the first image is determined based on use of the first image for the first patient. A machine trains a first network based on the ground truth and the first image. The medical imager is updated with the first machine-learned network from the machine training and applies the first machine-learned network for imaging a second patient. The medical imager generates a second image of the second patient. The second image is responsive to results of the applying of the machine-learned network.

In a second aspect, a method is provided for updating a medical scanner. The medical scanner images a first patient using a first machine-learned network. A ground truth for the imaging for the first patient from data generated by examination of the first patient is determined where the ground truth is a positive example. The medical scanner is updated with a second machine-learned network replacement of the first machine-learned network. The second machine-learned network having been trained based on the ground truth collected for the imaging of the first patient by the medical scanner. The medical scanner images a second patient using the second machine-learned network.

In a third aspect, a system is provided for machine learning in medical imaging. A medical scanner is configured to scan first patients. A processor is configured to determine ground truths for the scans of the first patient from indications of the ground truths in records of examinations of the first patients and to repeatedly train a machine-learned model based on the ground truths as feedback from the scans of the first patients. A display is configured to display images from the scans of the first patients. The images are responsive to the machine-learned model as trained when each of the images is generated. Different of the images are responsive to different versions of the machine-learned model.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An artificial intelligence (AI)-based self-learning and self-optimizing medical imaging scanner adapts to local practice and/or change in practice in a less costly and time-consuming manner than expert-based off-line retraining. The self-learning and self-optimizing smart medical device automatically learns from experience (i.e. gets better after repeated use). AI-based algorithms enable the scanner to "learn from experience" by constantly analyzing data that is produced by the device (and other connected devices) and incorporating the feedback from the human user of the device as ground truth. This smart scanner is equipped with a set of algorithms that can automatically seek out data and run experiments to train (or retrain) either new or existing models.

Figure 1:
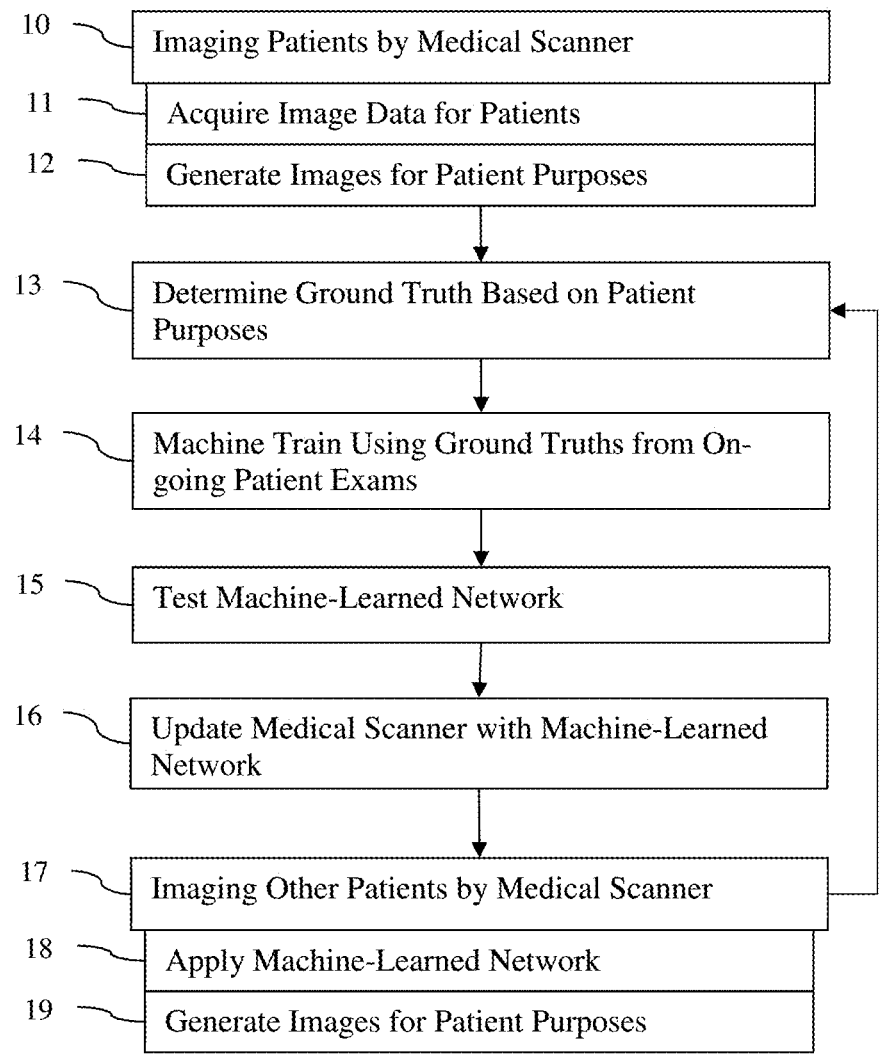
FIG. 1 is a flow chart diagram of one embodiment of a method for machine learning or updating a medical imager.

FIG. 1 shows one embodiment of a method for machine training with a medical imager and/or for updating a medical scanner. For examining a patient, one or more users of the medical imager or patient data from the medical imager interact with the imager or the medical record of the patient. This interaction for treatment, diagnosis, and/or prognosis of the patient indicates a ground truth for a sample that is the image and/or record for that patient. This ground truth is used to train or retrain a machine-learned network to be applied by the medical scanner for examination of other patients. This on-going training process provides self-learning and/or optimizing by the medical scanner without review or with limited review by an expert not connected with the patients.

The method of FIG. 1 is implemented by a medical imaging system. In one embodiment, the system of FIG. 3 implements the method of FIG. 1. For example, a medical scanner performs the imaging of acts 10 and 17. The medical scanner, workstation, or other processor determines the ground truth based on data created for patient purposes in act 13, machine trains in act 14, and/or tests in act 15. The medical scanner updates itself or another workstation or processor updates the medical scanner in act 16. Other devices may perform or be used in the performance of any of the acts.

The acts are performed in the order shown (top to bottom or numerical) or another order. For example, the testing of act 15 may be performed after the updating of act 16.

Additional, different, or fewer acts may be provided. For example, act 15 is not provided. As another example, act 10 is replaced with act 17 so that the looping feedback is from act 16 to act 17, such as where the update is to replace a previous machine-learned network with a more recently trained network.

In act 10, the medical scanner images patients. Any medical imager may be used. Example medical scanners include magnetic rasonance (MR), computed tomography (CT), x-ray, ultrasound, positron emission tomography (PET), single photon emission computed tomography (SPECT), pathology systems (e.g., an in-vitro diagnositics camera for viewing tissue on a slide), or other device for imaging inside or the surface of a patient.

The medical scanner images by scanning. Energy is transmitted to the patient, and the response is measured. Alternatively, emissions from the patient are detected. The patient is scanned at a point, along a line, over an area or plane, and/or in three dimensions. Any part of the patient may be scanned.

The medical scanner scans different patients. For each patient, the scan is for prognosis, diagnosis, and/or treatment of the patient. The patient is being scanned to help the patient. A treating physician orders the scan, a technician performs the scan, and a radiologist may review results of the scan. These users of the scanning are helping the patient, so the data is for patient purposes.

The scanning generates data. A log of the performance of the medical scanner for the scan, image data, an image, scan settings, and/or other data is generated by the medical scanner for the examination of the patient. Other data may be accessed or used for the examination, such as lab results, patient medical history, patient clinical data, data from a pressure and/or heart monitor (e.g., ECG), and/or other data. The data is gathered for the patients being treated or diagnosed by the medical facility and professionals.

Any imaging process may be used. In one embodiment, acts 11 and 12 are performed for imaging. In act 11, the medical scanner aquires image data representing the patient. The medical scanner provides medical data representing a region of the patient. The medical scanner may directly provide the image data, such as providing in an image processing pipeline of the medical scanner. The medical scanner may indirectly provide the image data, such as routing the image data through a memory or computer network. The image data may be accessed from a picture archiving and communications system (PACS) server or electronic medical record.

The medical scanner is configured for acquiring the image data. Values for various scan settings are set. The scan settings may control transmission, reception, or post-reception processing (e.g., filtering, detecting, and/or reconstruction). In one embodiment, a machine-learned network is used for acquiring the image data. For examle, the machine-learned network was trained to output scan settings to use based on patient-specific input data. Application of the machine-learned network to patient data provides values for the scan parameters. As another examle, the machine-learned network was trained to output a sequence of scanning or process to examine the patient. In alternative embodiments, a machine-learned network is not used for acquiring in act 11.

In act 12, the medical scanner generates one or more images of the patient from the image data. The measured signals from the patient are processed to generate an image. The image is scalar values that may be formatted and/or mapped to display values or is display values (e.g., RGB). Any image processing may be used, such as filtering, reconstruction, rendering, segmentation, and/or landmark detection. The image may include graphics, such as wireframes or outlines for detected landmarks or segmented objects.

In one embodiment, the generation of the image or images uses a machine-learned network. For examle, an anatomical landmark is detected with or by a machine-learned network. As another examle, an object (e.g., organ, lesion, or tumor) is segmented with or by a machine-learned network. In yet another example, image data representing a volume is three-dimensionally rendered to a two-dimensional image based on rendering settings output by a machine-learned network. In another example, the image data or image is filtered by application of a machine-learned network. A reinforcement-based network may provide a sequence of image processing. In an alternative, a machine-learned network is not used for generating the image or images.

In act 13, a ground truth is determined for the image or images generated for the patient. The ground truth is determined by the medical scanner, a workstation, server, or other computer.

The ground truth is an acceptance of an image, a rejection of the image, a final image after any changes, or other indication of use of the data for the patient (e.g., the end result from examination of the patient). Various data sources may be used to determine the ground truth, such as an image of the medical scanner, an image or scan settings from a PACS database, clinical guidelines, scanner log data in the medical scanner or a maintenance database, electronic medical record for the patient, data from other sensors, and/or other data. The data may be stored local to the medical scanner and/or remotely from the medical scanner.

The data is generated for the patient by the users of the medical scanner. The treating physian, nurses, scanning technician, radiologist, and/or other medical professional providing medical services to the patient generate the data. The ground truth is determined from the data created for patient purposes. For example, an image generated for patient examination is used for the patient, indicating acceptance of the image. The image and corresponding data for the patient examination indicate the ground truth. The ground-truth is inferred from other downstream events that the patient and/or the medical image encounters during the day-to-day clinical practice. There is not a dedicated process whereby the ground-truth is created for the purpose of training an algorithm. Rather, the ground-truth is created by the virtue of having access to other contextual data from the clinicians, IT systems, etc. for the patient. Some other (e.g., more implicit) ways of collecting the ground-truth are, for example, (1) the ground-truth whether a plaque seen in a CT scan of the coronary vessel is "risky" (vulnerable to rupture or not) is extracted from the patient's medical record which indicates whether a patient had an acute heart attack at a later date, (2) if a lesion detected on a mammography is malignant or benign may similarly be inferred from a downstream biopsy test, or (3) if an image is good quality of not can be inferred from the log files of the scanner which indicate whether the same imaging protocol was repeated in quick succession.

In one embodiment, input to the medical scanner and/or log data of the medial scanner is used. For example, the medical imaging scanner is equipped with a machine learning-based algorithm to detect anatomical landmarks on scout images (MRI) or topogram (CT) images for scan planning. A user can edit and/or over-rule these automatic detections and continue with the scan acquisition. Each time the user accepts, rejects, or edits the detections and/or use the detected landmarks information for self-tuning is determined as the ground truth. The edited detection, acceptance, and/or rejection for patient examination is a ground truth for the corresponding image or detection. The medical scanner may send the positive examples, negative examples, final edits, intermediate edits, or other ground truth to a master database where the detection algorithm may be re-trained and re-deployed on the scanner.

In another embodiment, the medical scanner queries the data on the PACS (either once, or in a regular fashion e.g. nightly). The image output by the medical scanner is compared to the image in the PACS. Where the image in the PACS is edited, an indication of a negative ground truth for the image of the medical scanner is provided, and an indication of a positive ground truth for the image of the PACS is provided. The corrected ground-truth (negative) and positive ground truth and corresponding images may be used to re-run the training algorithm. This re-trained network can then be deployed on the scanner automatically.

The indication of acceptance or change of an image for the patient may provide positive or negative ground truth for that image. The image after change may provide a positive ground truth. The acceptance may be indicated by storage of the image in the patient medical record, transfer of the image to PACS, log data indicating the image as the final or last image, or other indication of acceptance or not. For example, the log data may indicate repetition of the same scan or regeneration of the image from the same image data with one or more different settings. If within a threshold time and/or based on saving or transfer, the acceptance or rejection may be indicated.

In one embodimment, often several scans are repeated due to poor quality. There could be several reasons for the poor quality—operator error, motion artifact due to breathing and/or patient movement, incorrect contrast timing, etc. The medical scanner may be able to automatically detect the poor-quality scan and use the poor-quality image as a negative example in the ground-truth training database. The poor quality is indicated by rescanning, failure to save the image in the patient's medical record, overwriting of the image, log data, and/or a measure of image quality. For example, the repeat scan may be identified when an operator performs the exact same scan in succession within a threshold time. In such a case, the medical scanner assumes that the first scan was the poor quality (ground-truth label), while the next scan is of diagnostic quality (ground-truth label). In another example, the repeated scan is detected by the scanner by analyzing the usage log files that are produced by the scanner.

In another embodiment, the ground truth is determined from solicitation. The medical professional using results of the examination of the patient is queried by the medical scanner and/or other computer. The user interface for an image or other data includes a prompt for the user to indicate acceptance or rejection. For example, the medical scanner prompts the user to annotate an image (i.e. provide ground-truth) and then store this label for use during the algorithm training process.

Using the user interface, the medical scanner works collaboratively with the user or service department to update its parameters for a better performance, according to the history of user feedbacks. Following retraining, the scanner proposes to the user the upgrade that will increase the user satisfaction (i.e., the performance will be close to the user's feedback).

Various imaging examples are used above. In other embodiments, the examination process is used as the sample with the ground truth being for each act or completion of all the acts, such as for reinforcement learning. In yet other embodiments, the machine learning network is to learn to provide other information for patient examination, such as an amount of contrast agent used for generating an image. The amount of contrast material to be administered to a patient is typically calculated as part of the scan protocol. The amount is based on the patient's height/weight and kidney function as well as the imaging requirements. The medical scanner queries this data from the electronic medical record system and pre-computes some or all the parameters used to determine the total contrast volume. The amount used for a patient is labeled as a positive ground truth. Any proposed or rejected amounts not used are labeled as negative ground truth.

In one embodiment, the medical scanner may query similar patients from the PACS, who had the same scan, and train a model that computes the optimal amount of contrast agent needed to achieve diagnostic image quality.

The ground truth and corresponding example are used to train a network to output the amount. Alternatively, the training is to create alerts when an excessive amount of contrast material is being planned for a particular acquisition. For example, a patient with impaired kidney function may be automatically detected by the scanner by querying the kidney function related measurements from the EMR system. The trained network is used to identify whether the amount is excessive given the kidney function for the patient.

In act 14, a machine peforms machine training. The machine is a processor of the medical scanner, a server, a workstation, or a computer. Based on the training data (e.g., examples and ground truth), the artificial intelligence system is trained to produce the desired output from input data. The artificial intelligence or intelligence is machine trained. A machine, such as an image processor, computer, server, or other device, learns from the samples to provide an output. Using machine-learning, complex statistical relationships between large numbers (e.g., tens, hundreds, thousands, or more) of input variables to any number of output variables are extracted from the large number of samples based on the ground truth.

The training is for imaging in any context. One model may be learned for any number of imaging situations.

Alternatively, different models are trained for different situations. The different situations may include different scan modalities (e.g., different model for computed tomography, magnetic resonance, ultrasound, positron emission tomography, and single photon emission computed tomography). The different situations may include different types of tissue of interest (e.g., liver versus kidney), different diagnostic purpose or workflow (e.g., cancerous lesion versus bone calcification), and/or different users (e.g., different operators may have different preferences for visualization).

Figure 2:
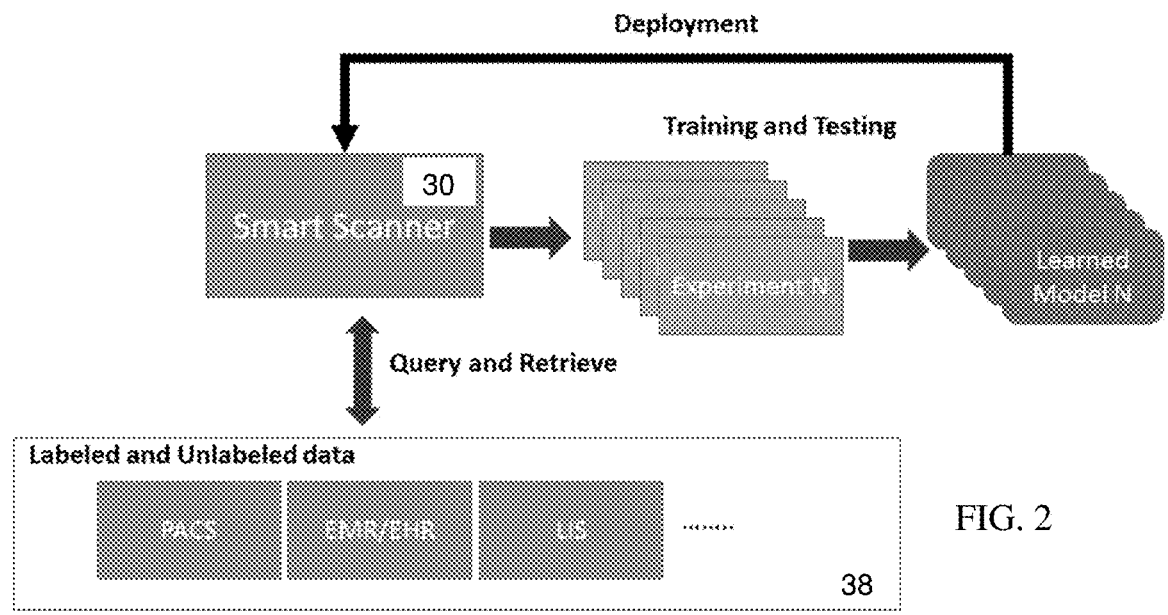
FIG. 2 illustrates self-learning or optimizing of a medical scanner.

FIG. 2 shows an example where the scanner 30 uses patient data from the database 38 (e.g., PACS, electronic health or medical record database, laboratory information system, and/or other data source) to collect any number N of datasets for training a corresponding number of models. The scanner may self-learn or self-optimize for different contexts and/or situations. The model is the output of the training/testing cycle for a given experiment. For example, if a deep neural network is used as the method of choice, then the model is the optimized weights and biases together with the network architecture. The experiment refers to the process whereby a model is trained and subsequently tested. Each experiment may have its own hypothesis and corresponding training data. Each experiment and corresponding model may have a same hypothesis but different training data.

Any now known or later developed machine learning may be used. Regression, classification, and/or reinforcement learning are used. Regression training learns a range or continuous output by minimization of a metric. Classification learns disparate outputs. Reinforcement learning learns a sequence of actions with feedback. Neural network, Bayes network, probabilistic boosting tree, or support vector machine training may be used. Hierarchal, cascade, or other approaches may be used. Supervised, unsupervised, or semi-supervised machine learning may be used.

To train, features are extracted from the input data. Haar wavelet, steerable, gradient, or other features may be extracted from the image data or images. Alternatively, the input data itself (e.g., pixel or color values of the rendered image) is used and the learning determines features, such as with deep learning. In deep learning, the training learns convolution kernels, weights, and/or connections from the input images to generate the output. Deep learning models high-level abstractions in data by using multiple processing layers with structures composed of multiple non-linear transformations, where the input data features are not engineered explicitly. The deep learning provides the features used by other machine training to learn to output. Other deep learned, sparse auto-encoding models may be trained and applied. The machine training is unsupervised in learning the features to use and how to classify given an input sample (i.e., feature vector). Any neural network architecture for the deep learning may be used. The neural network architecture defines the neural network used to train and the resulting trained or machine-learned comparison model.

The training is based on the ground truth and the corresponding data, such as the image or image data examples. The ground truth identified from the examination of the patient and the data from the examination of the patient are used in the training. The training data is gathered from one or more memories, sensors, and/or scanners. The gathered data may be stored and/or transmitted to a buffer, memory, cache, processor, or other device for training. This gathered training data is input to the machine learning algorithm.

Many samples of the same type of data are input. To learn statistical or other relationships that may be sufficiently complex that a human cannot perceive the relationships in a same level, tens, hundreds, or thousands of samples are provided. The samples from any previous training and newly acquired samples are used. Re-training may occur upon acquiring a single new sample and ground truth, periodically, after a given time, and/or after acquiring a threshold number of samples.

For training, the goal or ground truth information is input. The artificial intelligence system is trained with labeled data (e.g., input images with detected landmarks or segmentation). Only positive or positive and negative examples may be input. In other embodiments, a non-binary scalar is used as the ground truth, such as an amount or other indication of a level of contrast agent (e.g., whether the amount is safe for the patient).

The trained artificial intelligence is stored. The trained model is stored in a memory. Any memory may be used. The memory used for the training data may be used. For application, the memory may be in another device. For example, the trained model is stored in a memory of a medical imager or workstation. A server implementing one copy of the trained model may be used for different patients. Multiple copies of the trained model may be provided to different physicians, medical scanners, and/or workstations for use by different physicians for different patients.

In act 15, the machine-trained network is tested. The machine performing the training tests. Other machines may perform the testing.

Any testing may be performed. For example, some of the samples and corresponding ground truth are not used for training. Instead, the machine-learned network is applied to the data of these "held-back" samples. The output of the network is compared to the ground truth. The accuracy of the prediction may be calculated. As another example, one or more safety regulations are checked. The output of the machine-trained network is checked against any safety requirements. Where the network outputs values for scan settings, a model of the medical scanner using the values may be used to verify that saftey requirements for the energy or effects from the energy on the patient are satisfied.

Given the regulatory constraints, the trained model may be automatically deployed only when the model guarantees safety and efficacy requirements that may have been defined a-priori. In other instances, the trained models may require or prompt for human input, whereby a user or other makes the deployment decision.

In act 16, the medical scanner updates. The machine-learned network is added to the medical scanner. Alternatively, a refernce or call command to use the remotely stored machine-learned network is added to the medical scanner. The medical scanner uses the updated processor to apply the machine-learned network. In yet other alternatives, the update is of a processor other than the medical scanner.

The medical scanner automatically deploys the trained model. The deployment may be done on the scanner itself, or on other devices such as the reading workstation or the PACS workstation.

In one embodiment, a previously machine-learned network for the medical scanner is replaced by a re-trained machine-learned network. A network for a partcular application is replaced by another network for the same application. As the machine-learned network is used for patients, further examples and patient examination-based ground truths are collected. This collection of training data, with or without training data gathered for an earlier iteration of training, is used to re-train the network with machine learning. This leads to self-learning by the medical scanner based on use of the medical scanner for patients, as represented by the feedback from act 17 to act 13. In alternative embodiments, the update is to add the machine-learned network where there was not a previously used network for the same application.

The update is automatic. Based on a trigger (e.g., collection of a certain number of samples of training data or time) or based on user triggering, the machine training of act 15 is performed. Once the machine-learned network is trained, the update occurs without user intervention. Alternatively, the update occurs after testing shows an accuracy above a threshold level and shows satisfaction of any saftey or other regulations.

In other embodiments, the update is triggered by a user. For example, the test results are provided to a user for approval by the user before triggering the update. In another embodiment, the scanner follows a protocol for executing the update by getting one or more approvals. For example, the scanner contacts the service department, hospital administration, physician, or third party and asks for update approval. The update may be reversible, such as changing back to a previous iteration.

In act 17, the medical scanner images a patient. The imaging is performed as discussed for acts 10-12. The imaging is performed for diagnosis, prognosis, and/or treatment of the patient. The imaging is performed for any number of patients. Different patients are imaged at different times.

In act 18, the imaging uses the machine-learned network. The network may be used for acquisition, such as to estimate an amount of contrast agent to be used and/or values for scan parameters. The settings for post-processing or image processing may be output by the network and used. The network may be used for landmark detection and/or segmentation. Other uses in imaging may be provided. The network is applied to input data for the patient being scanned and outputs information used to image or extract from an image.

In act 19, the medical scanner generates an image of the patient. The image is generated as discussed above for act 12. Due to the application of the machine-learned network in the imaging of act 17, the image is responsive to results of the applying of the machine-learned network. The response may be a graphic or other indicator of a detected landmark or segmentation. The response may be of contrast agents, an amount for injection having been determined by the machine-learned network.

The generated image or images for each patient are displayed on a display screen. The physician and/or technician views the image for diagnosis, prognosis, and/or treatment of the patient. The user may save the image, alter the image, transmit the image, discard the image, and/or repeat the image acquisition. This interaction occurs on the medical scanner and/or after storage of the image at another locations (e.g., PACS or electronic health record). The interaction and/or other information generated for the purpose of the patient examination may be used to determine ground truth without expert review for the purpose of creating ground truth.

Figure 3:
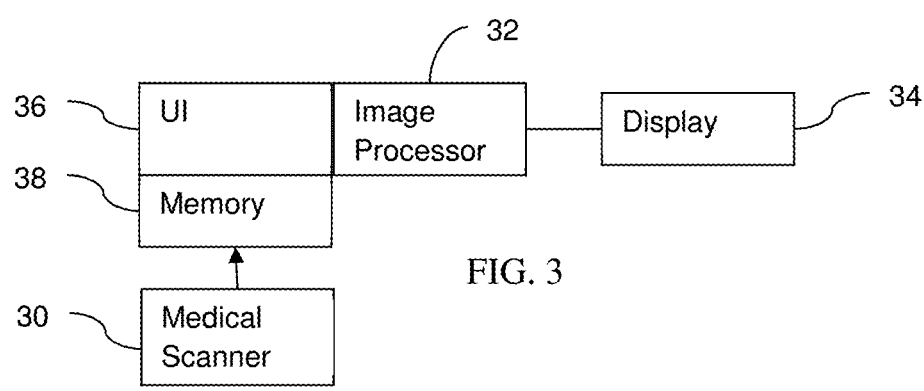
FIG. 3 is a block diagram of one embodiment of a system for machine learning in medical imaging.

FIG. 3 shows a block diagram of one embodiment of a system for machine learning in medical imaging. The system implements the method of FIG. 1 or 2, and/or another method for using day-to-day patient examination information to derive ground truth and train based on the derived ground truth. The system is for training with machine learning and/or application of the machine-learned model. Other methods or acts may be implemented, such as providing a user interface for approving, supervising training, examining a patient, and/or applying a learned model.

The system includes a user input 36, a memory 38, a display 34, a medical scanner 30, and an image processor 32. Additional, different, or fewer components may be provided. For example, the medical scanner 30 and/or memory 38 are not provided. In another example, a network or network connection is provided, such as for networking with a medical imaging network or data archival system (e.g., PACS).

The user input 36, memory 38, image processor 32, and/or display 34 are part of the medical scanner 30. Alternatively, the user input 36, memory 38, image processor 32, and/or display 34 are part of a server, workstation, or computer separate from the medical scanner 30. In other embodiments, the image processor 32 and/or memory 38 are part of a remote server for interacting with the medical scanner 30, which includes the remaining components. The user input 36, memory 38, image processor 32, and/or display 34 may be a personal computer, such as desktop or laptop, a workstation, a server, or combinations thereof. In yet other embodiments, the user input 36 and memory 38 are part of a separate computer from the image processor 32.

The medical scanner 30 is a medical diagnostic imaging system. Ultrasound, CT, x-ray, fluoroscopy, PET, SPECT, and/or MR systems may be used. The medical scanner 30 may include a transmitter and includes a detector for scanning or receiving data representative of the interior of the patient. Scan data is acquired and used for diagnosis or surgical planning, such as identifying a lesion or treatment location. In another embodiment, the medical scanner 30 is a camera or scanner used for imaging in a laboratory, such as imaging a tissue sample in a slide. Any in-vitro diagnostics scanner may be used.

The medical scanner 30 acquires scan data representing the patient. The medical scanner 30 is configured by settings, such as a preset and/or user-controlled settings, to scan the patient. The scan is a volume scan, planar scan, linear scan, or scan of a point.

In alternative embodiments, the medical scanner 30 is not provided, but previously acquired scan data for a patient is stored in the memory 38. In yet other alternatives, many medical images are provided in the memory 38 as the training data, which is gathered and stored in the memory 38 from the medical scanner 30 or other sources.

The user input 36 is a keyboard, buttons, sliders, knobs, mouse, track-ball, roller ball, touch pad, touch screen, and/or any other user input device or hardware. The user interacts with the system using the user input 36. The patient, treating physician for the patient, radiologist for the patient, and/or technician scanning the patient may interact with the medical scanner 30 and/or the image processor 32 as part of the examination of the patient. These selections, configuration, edits, acceptances, storage, transmission, or other actions for dealing with data about the patient (e.g., images from the medical scanner 30 scan of the patient) are received by the user input 36. The actions or results of the actions may be stored and/or transmitted.

The memory 38 is a graphics processing memory, a video random access memory, a random-access memory, system memory, cache memory, hard drive, optical media, magnetic media, flash drive, buffer, combinations thereof, or other now known or later developed memory device for storing training data, scan data, images, electronic health record, PACS data, scanner log information, extracted ground truth, machine-learning architecture, machine-learned network, and/or other information. The memory 38 is part of the medical scanner 30, part of a computer associated with the image processor 32, part of another system, a picture archival memory, or a standalone device. For storing the training data, the memory 38 is a database. Links to patient data for different patients and/or a collection of data from different patients is stored in the database. The database stores the training data, such as samples from different patients and determined ground truths for the samples.

The memory 38 or other memory is alternatively or additionally a non-transitory computer readable storage medium storing data representing instructions executable by the programmed image processor 32 for learning or applying the machine-learned model. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 32 is a computer, workstation, server, processor, or other device configured to determine ground truths, apply machine learning, apply a machine-learned model, test a machine-learned model, and/or image a patient. The image processor 32 is configured by software, hardware, and/or firmware. For learning, the image processor 32 is configured by one or more machine learning algorithms. For applying a learned model, the image processor 32 is configured, in part, by a learned matrix or other data associating input data to output values.

The image processor 32 is configured to determine ground truths for the scans of patients. This determination is made after completion of examination for each patient, such as triggering at the end of an examination and before performing a next examination for a different patient. The medical scanner 30 may make the determination during examination or after completion of examination. Alternatively, another machine accesses output of the medical scanner 30 to make the determination during or after completion of the examination. The determination may be performed as a batch process, such as daily, weekly, or monthly, for examinations performed since the last implementation of the batch process. The image processor 32 may determine the ground truth from data in the database (e.g., memory 38), such as a PACS or electronic medical record and/or from data in the medical scanner 30.

The image processor 32 uses the data from the patient examination to determine the ground truth. Rather than having an expert review each case, indications of the ground truth are extracted from the data for the patient. Information from the medical professionals treating the patient is used. Such information includes inputs by the medical professionals, use of image and/or other data, log files, patient-specific data (e.g., history, lab results, and/or clinical data), and/or actions for acquiring the data. For example, the image processor 32 determines the ground truth for one or more images from user input on the user input 36.

The image processor 32 is configured to train a machine-learned model. The determined ground truths are used as feedback from the scans of the patients. This training data is used in machine learning to train the model.

The image processor 32 is part of the medical scanner 30 for training. Alternatively, the image processor 32 is a server or other processor remote from the medical scanner 30 but has access to data from the medical scanner 30. Training data is gathered from the on-going or day-to-day usage of the medical scanner 30 for patient purposes, and then a model is trained from the gathered training data with machine learning. That trained model may then be implemented by the very medical scanner 30 used to gather at least some of the data and/or other medical scanners.

Since the machine-learning is based on scanning patients as part of a medical practice to treat the patients, training data is regularly available or created. The training may be repeated when triggered or periodically. The repetition uses past training data as well as newly or recently acquired training data. A temporal window may be applied so that only training data within a threshold period from the current training is used. As a result of using recent examples, the re-trained machine-learned model is updated to reflect current and/or local practice.

The image processor 32 and/or the medical scanner 30 implements the machine-learned model. For a given patient, the input data is gathered and applied to the machine-learned model. The machine-learned model outputs a result or results, such as a detected landmark, segmentation, or amount of contrast agent. The results are used for the patient, such as to assist a physician in treatment planning, diagnosis, or prognosis.

The display 34 is a monitor, LCD, projector, plasma display, CRT, printer, or other now known or later developed device for displaying the rendered image or images. The display 34 is configured by a display plane memory or buffer, from which data is read to generate the image on the display screen. The display 34 receives images from the memory 38, image processor 32, or medical scanner 30. The images of the tissue captured by the medical scanner 30 are displayed. Other information may be displayed as well, such as generated graphics, text, or quantities as a virtual overlay.

The image and/or other information may be responsive to a machine-learned model. For example, images from scans of patients are displayed. These images are responsive to the machine-learned model as trained. The image may show a detected landmark, show data for a segmented object, may be colored to show the segmentation, may be responsive to scan settings used to acquire the image, may be responsive to an amount of contrast agent or contrast agent safety check, and/or may be responsive to other outputs from the machine-learned model.

When a given patient is examined, the currently existing machine-learned model is applied. The result is patient data or output responsive to the machine-learned model at that time. Since the model may be retrained, a different model is used for later patients. For example, different images are responsive to different versions of the machine-learned model.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for machine learning with a medical imager, the method comprising:
    acquiring, by the medical imager, first image data representing a first patient;
    generating, by the medical imager, a first image of the first patient from the first image data;
    determining a ground truth for the first image based on use of the first image for the first patient;
    machine training, by a machine, a first network based on the ground truth and the first image;
    updating the medical imager with the first machine-learned network from the machine training;
    applying, by the medical imager, the first machine-learned network for imaging a second patient; and
    generating, by the medical imager, a second image of the second patient, the second image being responsive to results of the applying of the machine-learned network.

2. The method of claim 1 wherein acquiring the first image data comprises acquiring using application of a second machine-learned network, and wherein updating comprises replacing the second machine-learned network with the first machine-trained network.

3. The method of claim 1 wherein generating the first image comprises generating using application of a second machine-learned network, and wherein applying the first machine-trained network comprises applying with the first machine-trained network replacing the second machine-learned network.

4. The method of claim 1 wherein determining the ground truth comprises identifying acceptance of the first image or a change to the first image.

5. The method of claim 1 wherein determining the ground truth comprises determining from input to the medical imager or determining from data stored in an electronic health record or picture archiving and communications system.

6. The method of claim 1 wherein determining comprises determining the ground truth from solicited user indication in a user interface.

7. The method of claim 1 wherein machine training comprises machine training with a supervise, semi-supervised, or unsupervised machine training.

8. The method of claim 1 wherein machine training comprises machine training by the medical imager.

9. The method of claim 1 wherein machine training comprises machine training based on the ground truth, the first image, and data for the patient.

10. The method of claim 1 further comprising testing the first machine-trained network, and wherein updating comprises updating after the testing.

11. The method of claim 1 wherein generating the first image comprises detecting an anatomical landmark with a second machine-learned network, and wherein determining the ground truth comprises detecting acceptance, editing, or rejection of an output of the detecting as the ground truth.

12. The method of claim 1 wherein acquiring comprises acquiring with first scan settings based on application of a second machine-learned network, and wherein determining the ground truth comprises detecting a repeat scan with second scan settings after generating the first image, the ground truth comprising a negative label for the first image and a positive label for a third image from the repeat scan with the second scan settings.

13. The method of claim 1 wherein determining the ground truth comprises determining an amount of contrast agent used for generating the first image, and wherein machine training comprises machine training the first machine-learned network to output an indication about a level of contrast agent.

14. A method for updating a medical scanner, the method comprising:
    imaging, by the medical scanner, a first patient, the imaging of the first patient using a first machine-learned network;
    determining a ground truth for the imaging for the first patient from data generated by examination of the first patient, the ground truth comprising a positive example;
    updating the medical scanner with a second machine-learned network replacement of the first machine-learned network, the second machine-learned network having been trained based on the ground truth collected for the imaging of the first patient by the medical scanner; and
    imaging, by the medical scanner, a second patient, the imaging of the second patient using the second machine-learned network.

15. The method of claim 14 wherein the imaging of the first patient and the imaging of the second patient are for diagnosis, prognosis, and/or treatment of the first and second patients, and wherein determining comprises collecting an indication of acceptance or change to a first image from the imaging of the first patient.

16. The method of claim 14 wherein determining comprises receiving prompted user indication of the ground truth.

17. The method of claim 14 wherein determining comprises collecting from log data of the medical scanner and/or electronic medical record of the first patient.

* * * * *